(12) United States Patent
Kringlebotn et al.

(10) Patent No.: US 7,072,044 B2
(45) Date of Patent: Jul. 4, 2006

(54) APPARATUS FOR ACOUSTIC DETECTION OF PARTICLES IN A FLOW USING A FIBER OPTIC INTERFEROMETER

(75) Inventors: Jon Thomas Kringlebotn, Trondheim (NO); Erlend Rønnekleiv, Trondheim (NO); Sverre Knudsen, Trondheim (NO)

(73) Assignee: Optopian AS, Trondheim (NO)

( * ) Notice: Subject to any disclaimer, the term of this patent is extended or adjusted under 35 U.S.C. 154(b) by 280 days.

(21) Appl. No.: 10/363,760

(22) PCT Filed: Aug. 30, 2001

(86) PCT No.: PCT/NO01/00352

§ 371 (c)(1),
(2), (4) Date: Sep. 8, 2003

(87) PCT Pub. No.: WO02/23169

PCT Pub. Date: Mar. 21, 2002

(65) Prior Publication Data

US 2004/0033017 A1 Feb. 19, 2004

(51) Int. Cl.
*G01B 9/02* (2006.01)

(52) U.S. Cl. ...................... 356/477; 356/450; 356/502; 73/61.75; 73/64.53; 73/28.01; 73/24.03

(58) Field of Classification Search ................ 356/502, 356/477, 35.5, 450; 73/61.75, 24.03, 657, 73/655, 28.04, 28.05, 61.79, 64.53, 865.5
See application file for complete search history.

(56) References Cited

U.S. PATENT DOCUMENTS

| | | | |
|---|---|---|---|
| 3,841,144 A * | 10/1974 | Baldwin | 73/61.75 |
| 3,906,780 A * | 9/1975 | Baldwin | 73/61.75 |
| 5,625,724 A | 4/1997 | Frederick et al. | |
| 5,767,411 A * | 6/1998 | Maron | 73/705 |
| 5,844,927 A | 12/1998 | Kringlebotn | |
| 6,233,374 B1 * | 5/2001 | Ogle et al. | 385/13 |

FOREIGN PATENT DOCUMENTS

| | | |
|---|---|---|
| DE | 42 24 744 | 2/1994 |
| GB | 2 284 256 | 5/1995 |
| SU | 1638580 | 3/1991 |

* cited by examiner

*Primary Examiner*—Hwa (Andrew) Lee
*Assistant Examiner*—Marissa J Detschel
(74) *Attorney, Agent, or Firm*—Patterson & Sheridan, L.L.P.

(57) ABSTRACT

Fiber optic particle detector for measurements in a fluid flow, comprising an optical fiber (2,3,12) being acoustically coupled to a mechanical element (11,13,14) adapted to be acoustically coupled to the flow, a fiber optic interferometer (54,56) and a light source (12,51,55) providing light in said optical fiber.

74 Claims, 8 Drawing Sheets

Figure 1A:
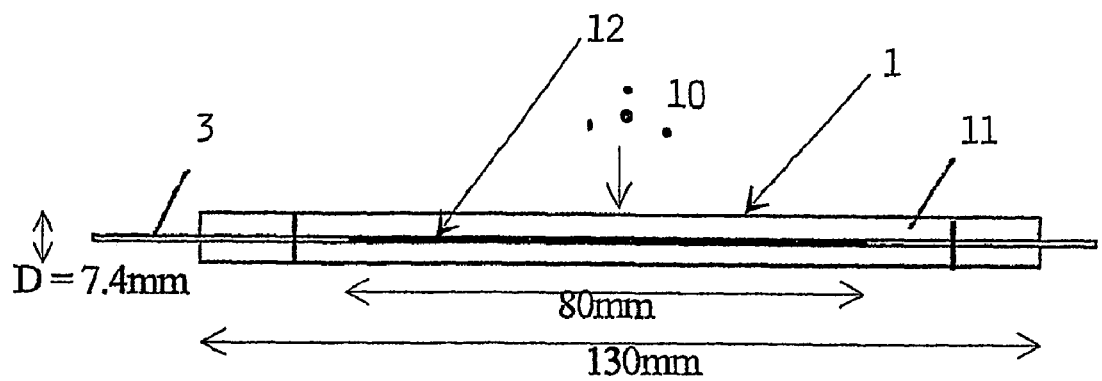

APPARATUS FOR ACOUSTIC DETECTION OF PARTICLES IN A FLOW USING A FIBER OPTIC INTERFEROMETER

This invention relates to an apparatus for detection of particles in a liquid/gas flow using a fibre optic interferometer.

BACKGROUND

Sand production in oil and gas wells is a serious problem mainly due to sand induced erosion. It is therefore of great interest to accurately detect the presence of sand and the amount of produced sand to maximise the oil/gas production rate and still maintain sand-free production.

Sand can be measured either with intrusive sensors, i.e. obstructions in the oil/gas flow, or with non-intrusive sensors. Intrusive sensors can either be based on measuring the erosion of the obstruction/probe, or on measuring the acoustic emission generated when the particles hit the obstruction. Conventional non-intrusive sensors are based on ultrasonic (PZT) transducers mounted at bends in the pipe, where particles will impact the inside of the pipe wall, generating an ultrasonic pulse which is picked up by the acoustic sensor. Non-intrusive sensors are much preferred unless intrusive sensors can offer significantly better performance. However, non-intrusive sensors will require bends, and are believed to be less sensitive than intrusive sensors.

Acoustic sensors should be able to measure acoustic signals at frequencies >100 kHz, or ideally >500 kHz, where sand noise is dominant over other noise sources, to provide unambiguous sand monitoring with high signal-to-noise ratio. Other noise sources include flow generated noise, mechanical/structural noise and noise from electrical equipment (eg. from electrical submersible pumps). Provided the individual hits can be separated in time, the quantity of produced sand can be derived from the number of hits and the signal amplitudes resulting from each hit. To be able to reliably detect sand particles and verify sand-free production with acoustic sensors, extreme sensitivity with large signal-to-noise ratio is required. Sand particles of interest have diameters ranging from 50–400 micrometers.

Fibre optic interferometric sensors are known to offer high sensitivity and resolution for dynamic measurands, which make them particularly attractive for acoustic sensing, eg. as hydrophones, see for example [T. G. Giallorenzi et.al., "Optical fiber sensor technology," IEEE J. Quantum Electron., Vol. 18, pp. 626–665, 1982]). The small dimensions of an optical fibre provide the potential for high frequency acoustic sensing, and the use of fibre optic interferometric sensors for ultrasonic acoustic sensing has been investigated [N. Lagaros et.al. "Ultrasonic acoustic sensing," Proc. SPIE, Vol. 798, pp. 94–101, 1987], [D. Wiesler et.al., "Fiber optic ultrasound sensors for medical imaging applications", 12th Intern. Conf. on Optical Fiber Sensors, Willamsburg, USA, pp. 358–361, 1997.]. A fibre optic interferometric sensor typically consists of two optical paths, where the optical path length difference is modulated by the measurand. The interferometer is normally excited by a laser source and the changes in differential optical path length causes a modulation of the light intensity at the output of the interferometer. It is known that the sensitivity and resolution is improved by using a high coherence laser source.

One known high coherence laser source is the fibre distributed feedback (DFB) laser [U.S. Pat. No. 5,771,251 to J. T. Kringlebotn et.al.], which consists of a single fibre Bragg grating providing feedback in a gain fibre, typically an erbium-doped fibre pumped by a semiconductor laser. Such a laser typically has a coherence length of several kilometers. It is further known that such a laser also can be used as a sensor element [U.S. Pat. No. 5,844,927 to J. T. Kringlebotn], for example for acoustic sensing, where the acoustic field modulates the stresses in the fibre laser and hence the optical frequency of the fibre laser, which can be measured using an optical interferometer which converts the frequency fluctuation into intensity fluctuations. The low coherence length of the laser allows the use of large path length imbalance in the interferometer and hence a high sensitivity. It is known that several fibre DFB lasers can be wavelength multiplexed along one optical fibre. Finally, it is also known that several interferometric sensors can be multiplexed along one or several optical fibres, for example by using Fabry-Perot type interferometers based on pairs of low-reflectivity FBG reflectors, where each pair has a different Bragg wavelength.

Fibre optic sensors are passive, with no electrical parts/wiring, and can provide reliable operation at high temperatures up to at least 200° C. The large bandwidth of an optical fibre also means that an almost unlimited amount of high frequency raw data can be transmitted along the fibre.

Interferometric techniques combined with high coherent sources allow highly sensitive dynamic measurements with low noise, hence providing good signal-to-noise ratio measurements. The potentially small dimension of these fibre optic sensors, in particular the DFB fibre laser sensor, allows for high frequency acoustic sensing [D. Thingbø, E. Rønnekleiv, and J. T. Kringlebotn, "Intrinsic distributed feedback fibre laser high-frequency hydrophone," Techn. Dig., Conf. on Bragg gratings, Photosensitivity, and Poling in Glass Waveguides," pp. 57–59, Florida, US, Sep. 23–25, 1999].

OBJECTIVE

The main objective of the present invention is to provide a reliable method and apparatus for high resolution detection of particles present in a liquid and/or gas flow in harsh environments with high temperature and/or pressure, such as encountered down-hole in an oil and gas well.

In particular the objective is to provide a reliable method and apparatus for permanent downhole detection of sand particles to determine the amount of produced sand from oil and gas wells to maximise the oil/gas production rate and still maintain sand-free production.

A further objective is to provide a method and apparatus for multi-point/distributed particle detection, which is very attractive for permanent downhole multi-zone sensing of sand production in a multi-zone well.

INVENTION

The objectives stated above are obtained using a particle detector characterized as stated in the independent claims. The main part of the invention comprises the use of at least one optical fibre attached to or embedded in a mechanical transducer element where particles hitting this element or a mechanical structure in physical contact with the transducer element generate high frequency acoustic waves causing a modulation of the stresses, and hence the optical path length and/or the birefringence in the optical fibre attached to the transducer element.

The transducer element can be hit directly by the particles to be detected, which will be the case if the element is an intrusive element placed fully or partly inside a pipe where the flow contains the particles to be detected. Alternatively the transducer element can be non-intrusive by clamping it to a mechanical structure, for example at a bend of a pipe, where the particles in the flow inside the pipe will hit the pipe wall generating acoustic waves which are picked up by the transducer element.

In the following the invention will be described with reference to the accompanying drawings, illustrating the invention by way of examples.

Figure 1B:
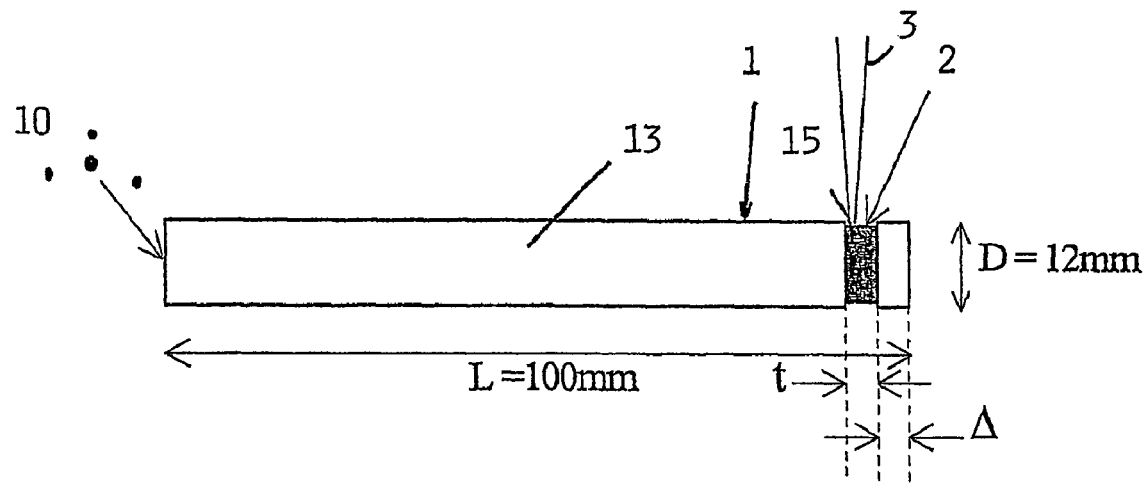
Figure 1C:
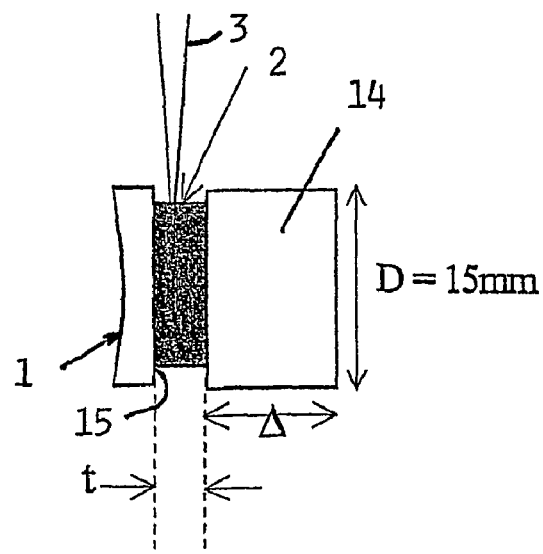

FIGS. 1A–C illustrate three different embodiments of the invention being adapted for intrusive or non-intrusive coupling to the flow.

Figure 2A:
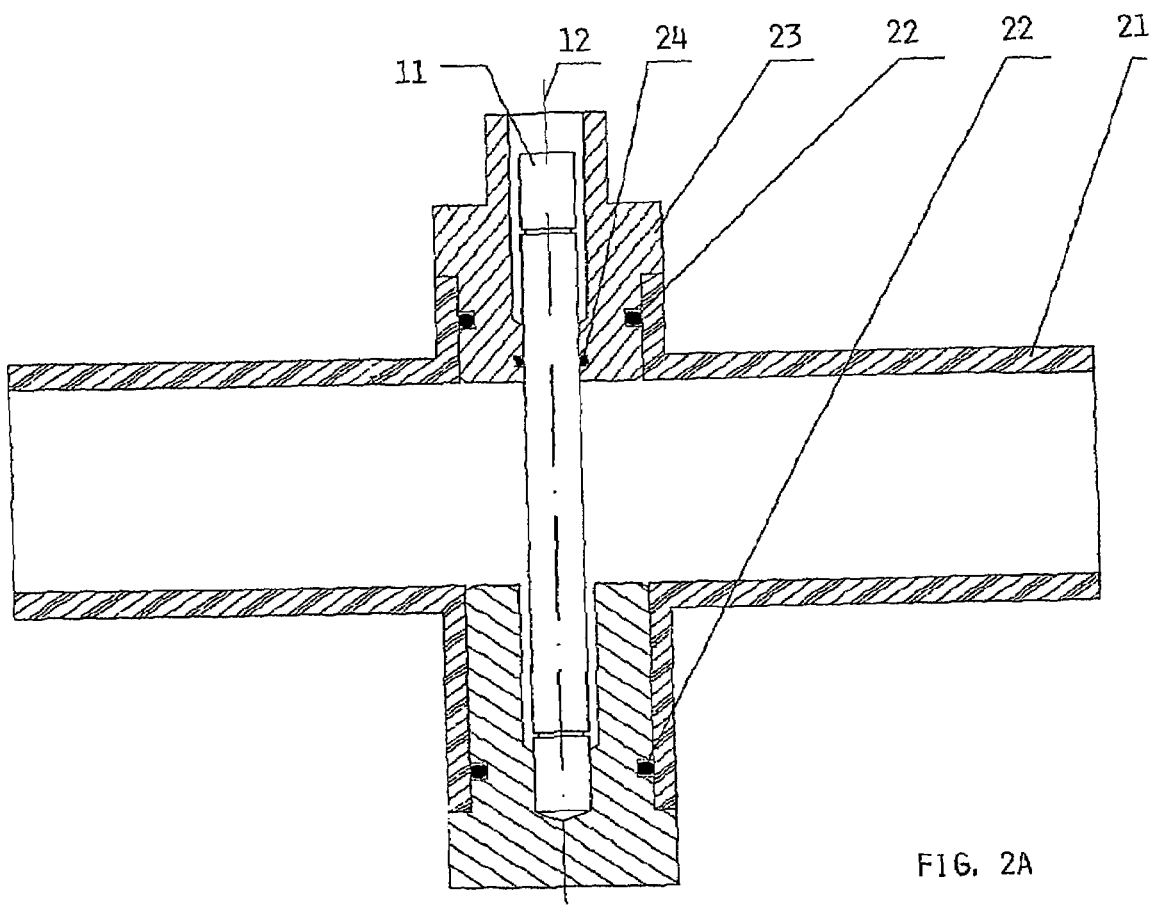
Figure 2B:
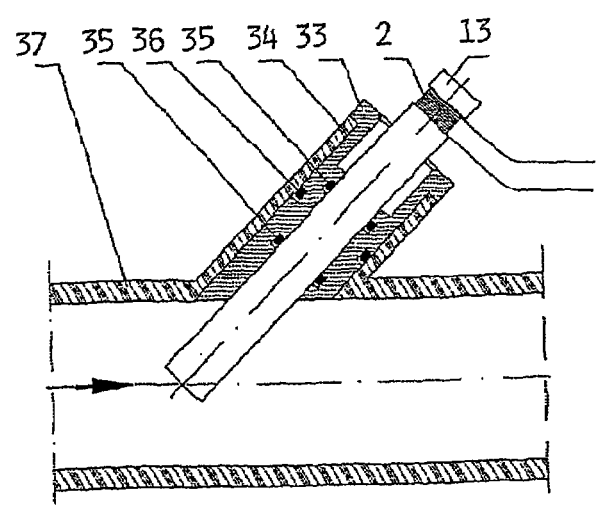
Figure 2C:
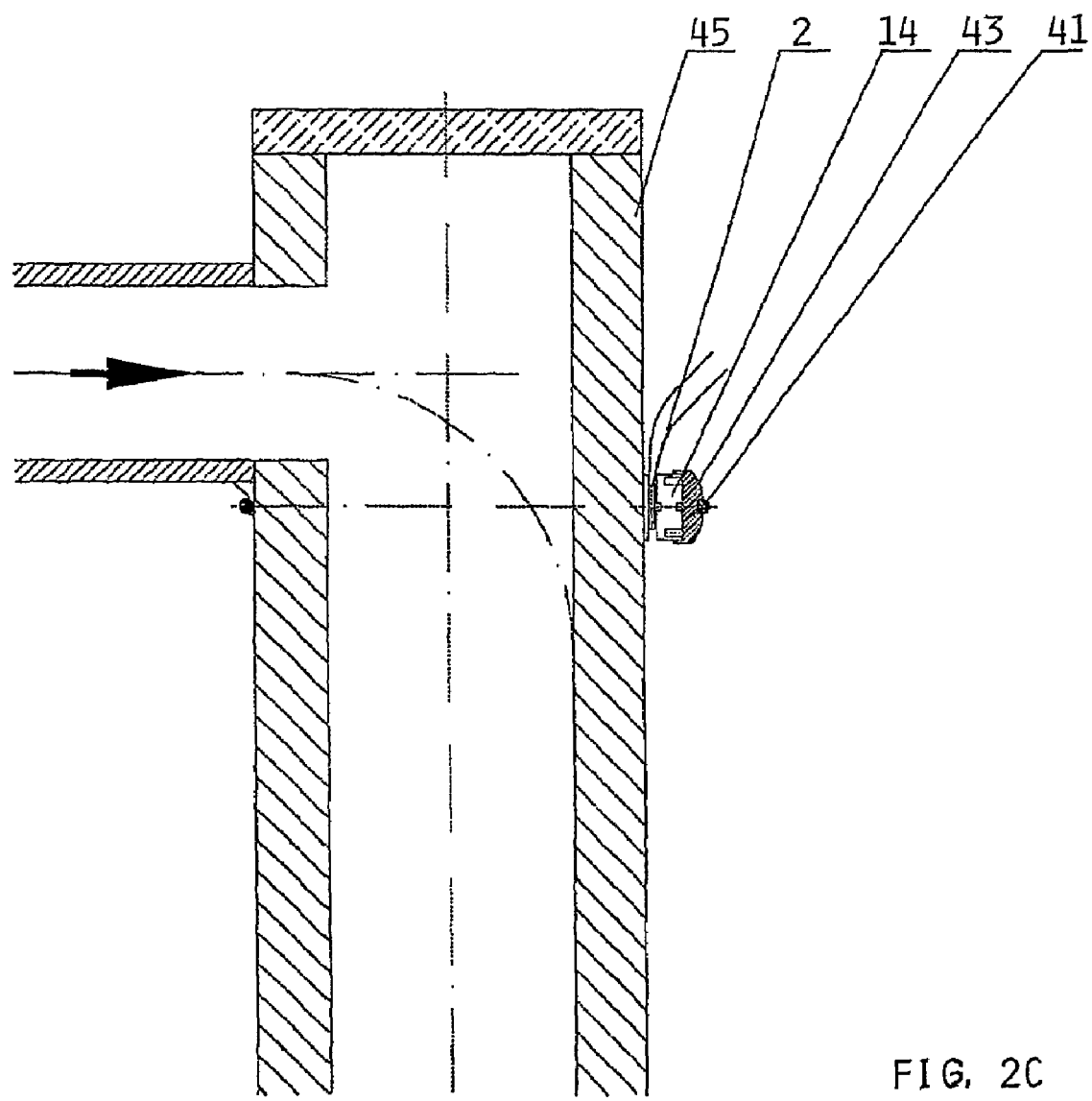

FIGS. 2A–C illustrates the positioning of the three embodiments of the invention in or on a pipe.

Figure 3A:
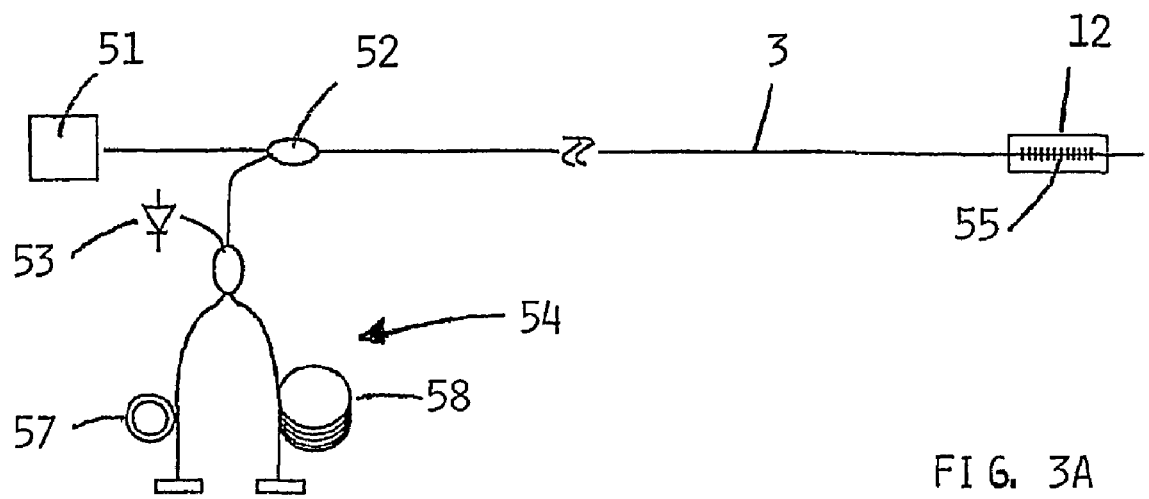
Figure 3B:
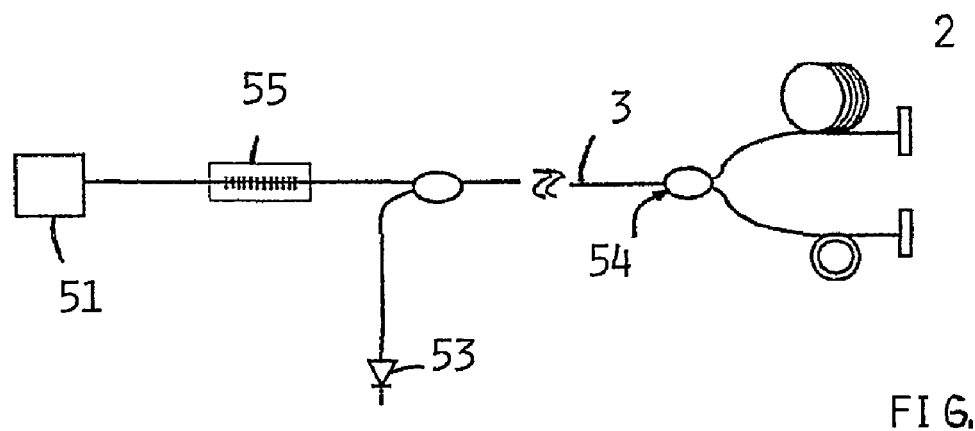
Figure 3C:
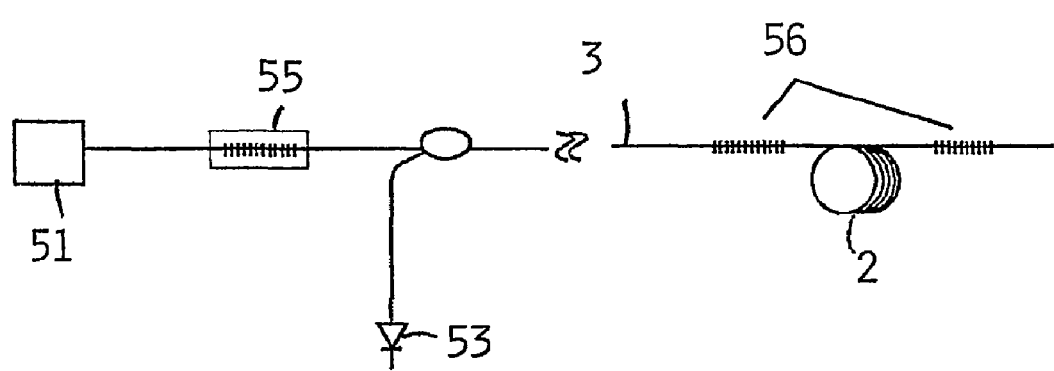

FIGS. 3A–C illustrates alternative optical fibre systems for detecting the vibrations generated by the particles in the flow.

Figure 4A:
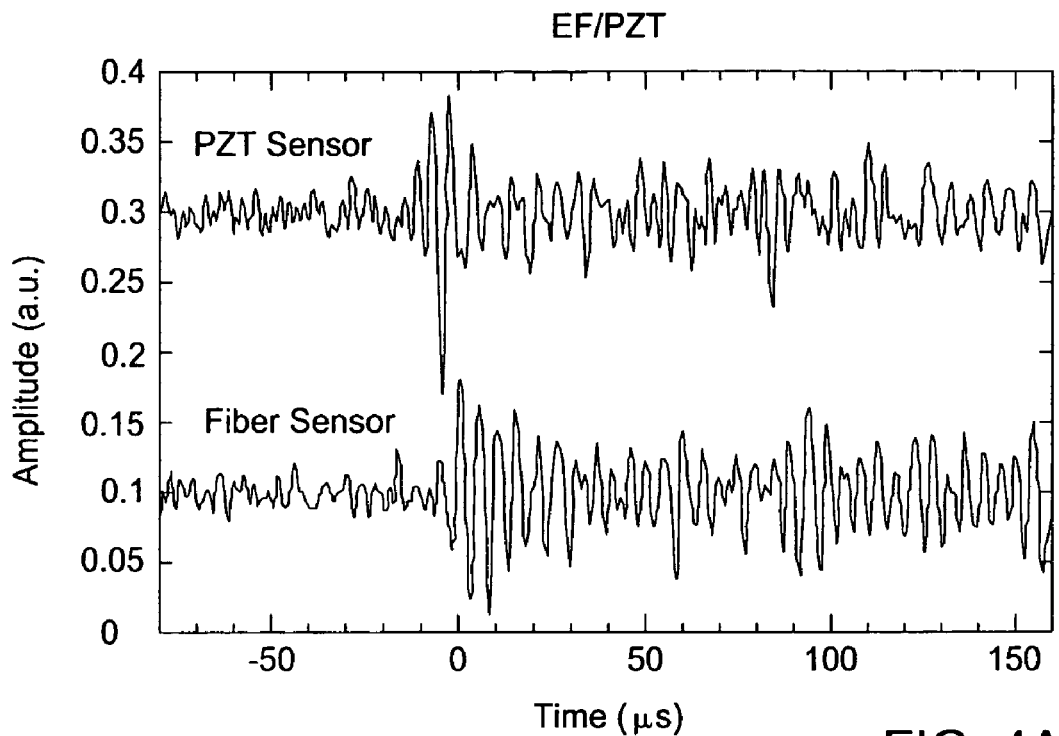
Figure 4B:
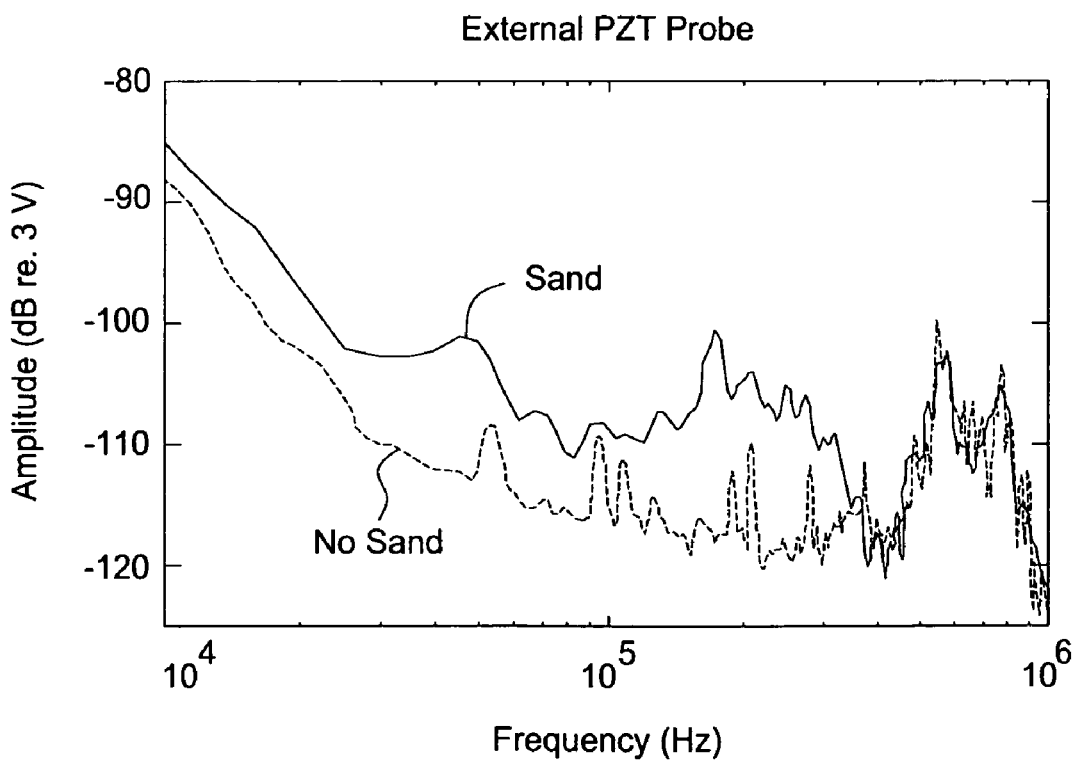
Figure 4C:
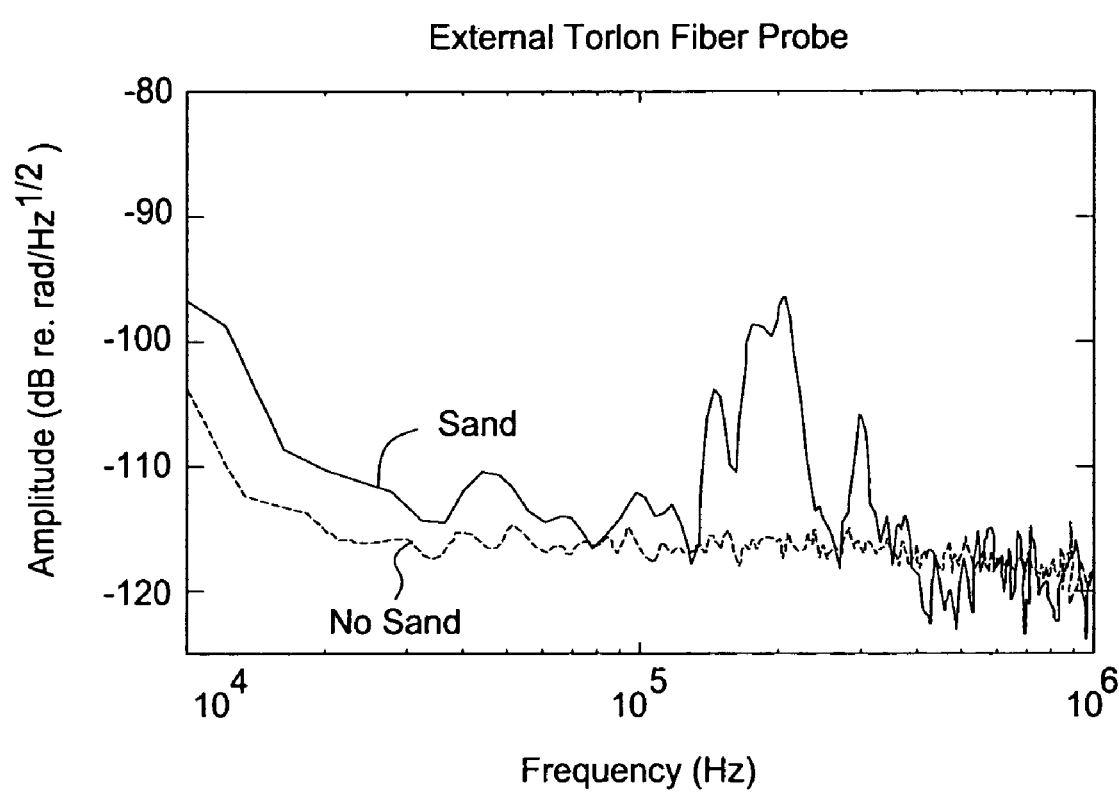

FIGS. 4A–C illustrating examples of measurements using the embodiment according to FIG. 1C.

Figure 5A:
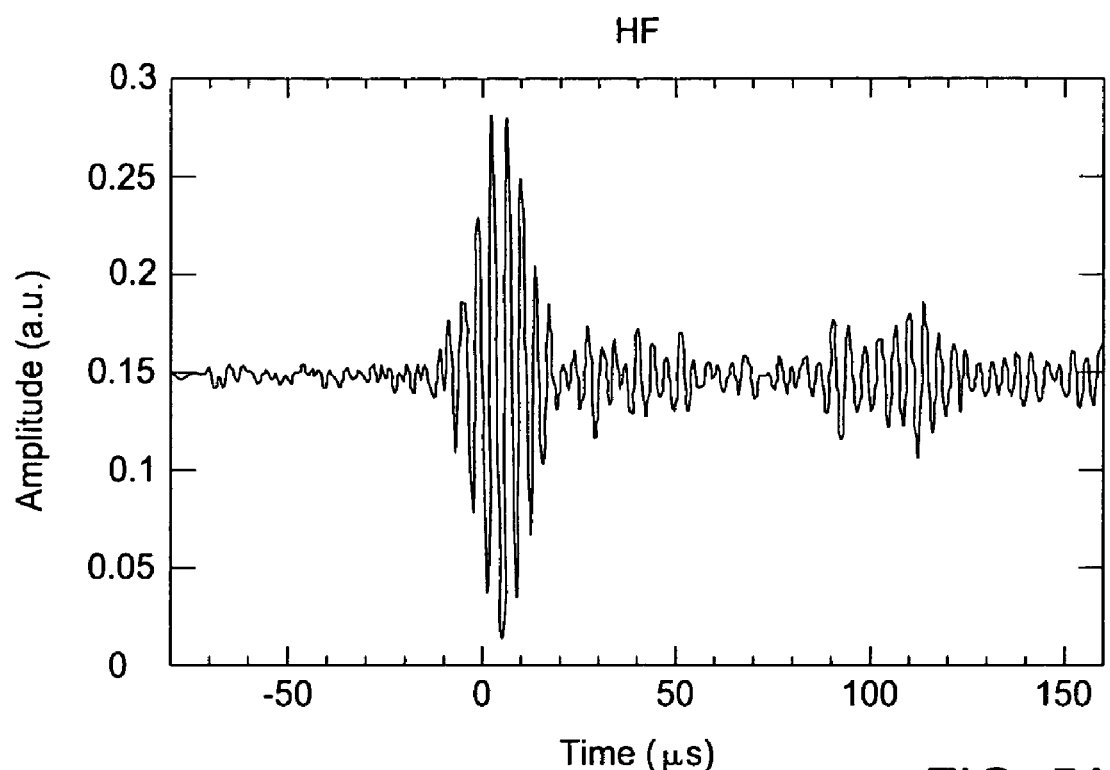
Figure 5B:
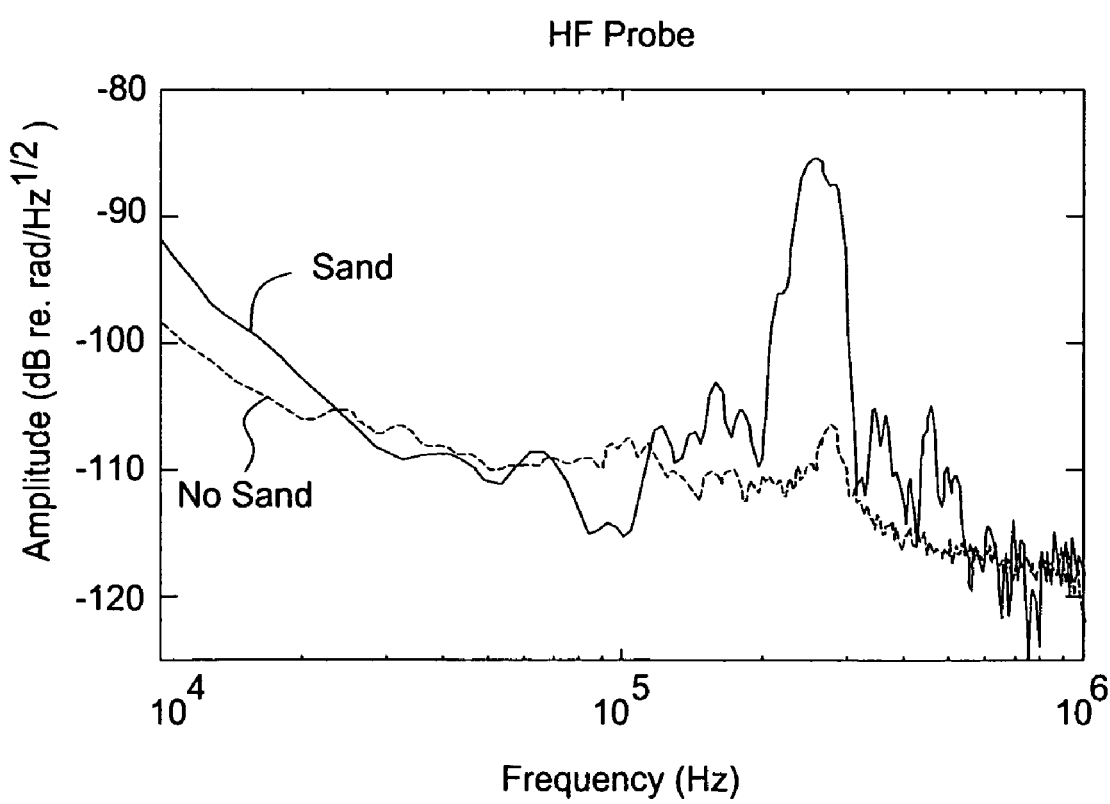

FIGS. 5A–B illustrating examples of measurements using the embodiment according to FIG. 1B.

Figure 6A:
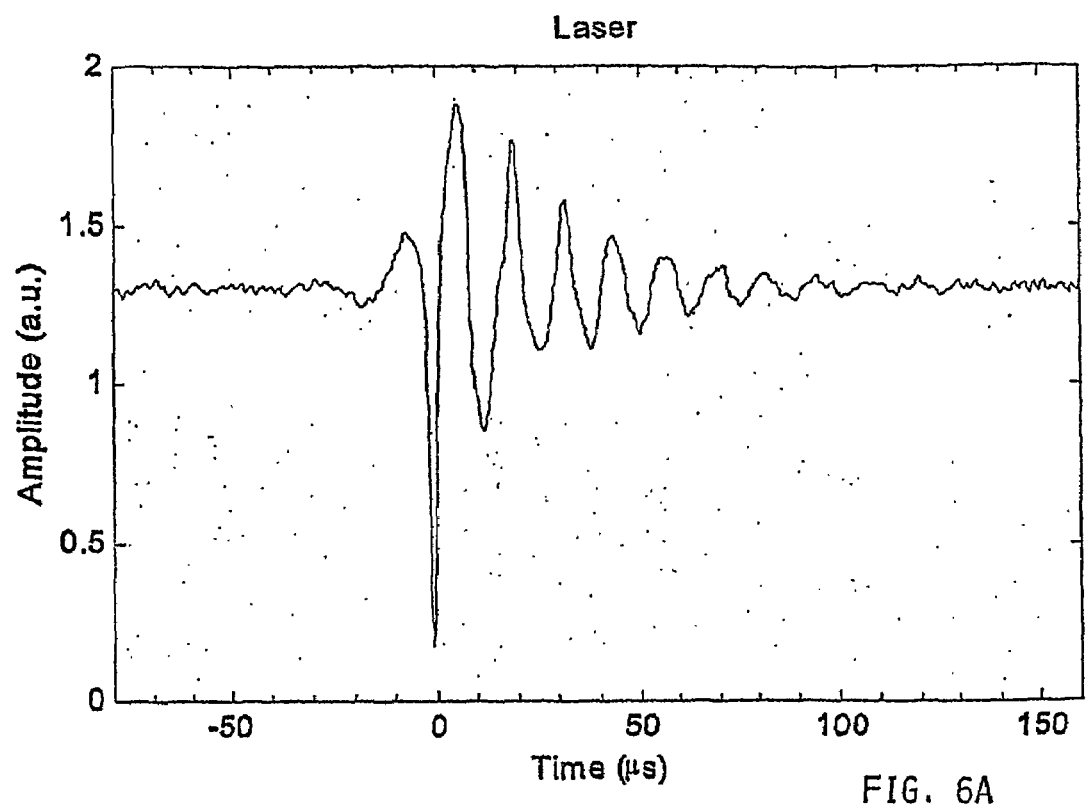
Figure 6B:
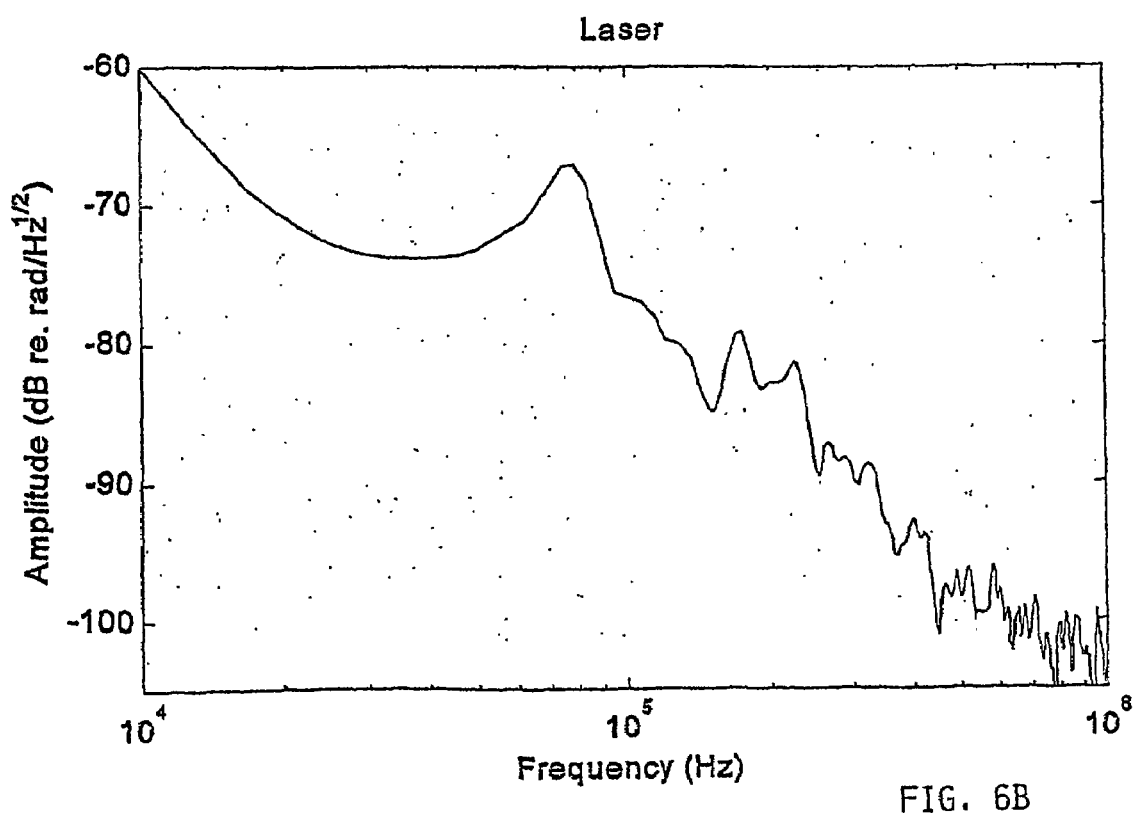

FIGS. 6A–B illustrating examples of measurements using the embodiment according to FIG. 1A.

FIG. 1 shows a schematic illustration of basic experimental transducer designs:

a) Intrusive fibre laser sensor transducer, using a fibre DFB laser 12, where the laser fibre is placed in a hole at the centre of a 13 cm long steel rod 11 having a diameter of 7.4 mm, and the hole is filled with silicon oil. The probe 1 is made to go through a flow pipe at 90°, as illustrated in FIG. 2A, with the centre of the laser at the centre of the pipe, such that the sand particles hit the probe at 90°. The particles 10 hitting the probe wall will set up ultrasonic waves in the probe modulating the stresses in the fibre laser and hence the laser frequency.

b) Intrusive interferometric sensor transducer, consisting of a 10 cm long solid steel cylinder 13 having a diameter of 12 mm, with a sensing fibre 2 coiled around the cylinder 13 inside a 1 mm deep square groove 15 with a width t=3–6 mm, positioned at a distance D=2–5 mm from the end surface. The probe 1 is inserted into the flow through the pipe wall at an angle of 45°, as illustrated in FIG. 2B, with the fibre coil end outside the pipe wall. The intrusive probe is based on acoustic wave pulse propagation along the cylindrical steel excited by sand particles hitting the end of the probe which is inside the pipe. The probe will theoretically be a single mode acoustic waveguide for acoustic frequencies $f_c < V_T/D$, where $V_T$ is the sound shear velocity in the material, which for steel is ca. 3200 m/s, implying that $f_c$ (for a cylinder diameter of D=12 mm) is ca. 270 kHz. The propagation pressure waves inside the waveguide will induce some radial expansion of the cylinder. This will cause a strain modulation of the fibre coil, which can be measured optically. Due to interference between the forward and backward propagating waves at the end of the probe there will be a resonance when the distance from the end face to the centre of the fibre coil equals a quarter of the acoustic wavelength $l_a$, i.e. when $l_a/4 = D + t/2$.

c) Non-intrusive interferometric sensor transducer consisting of a cylinder 14 with a fibre coil 2 wrapped around the cylinder inside a groove 15. The material of the fibre coil section is Torlon, which is a plastic material chosen to enhance the radial expansion due to the acoustic pressure wave. Other materials can be used, including steel. The transducer is clamped at the outside of a flow pipe near a bend, as illustrated in FIG. 2. The inner section is slightly curved to give better contact with the pipe, and a gel is used to improve the acoustic transfer of energy. The groove cylinder is made of Torlon, which is plastic material chosen to enhance the radial expansion due to the acoustic pressure wave. The outer section is made of steel and has a thickness D=6 mm.

FIGS. 2A–C illustrate the positioning of the three embodiments of the invention in or on a pipe. The embodiments can be used in a low pressure, low temperature test water flow loop. More complex embodiments have to be used in a real high temperature, high pressure oil and gas well, using high pressure seals and high temperature materials.

FIG. 2A illustrates the positioning of the intrusive fibre laser sensor transducer 11,12 shown in FIG. 1A in a pipe 21 with a water and sand flow. O-rings 22 are placed between the pipe and the transducer house 23 as pressure seals to prevent the water to penetrate out of the pipe and also for acoustic damping. In a real high pressure oil-well applications high-pressure-seals are required. O-rings 24 are also used between the transducer house and the steel transducer 11 containing the fibre laser 12 to acoustically decouple the transducer from the housing and the pipe. In this case the fibre is terminated inside the transducer, but a pass-through device with access to both ends of the fibre laser, which is necessary for multiplexing of several sensors along one fibre can be realised.

FIG. 2B illustrates the positioning of the intrusive interferometric sensor transducer 2,13 shown in FIG. 1B in a pipe 37 with a water and sand flow in the direction of the arrow. The transducer 2,13 is placed at an angle of 45° to the flow direction. The optical fibre coil 2 is positioned outside the pipe. As in FIG. 2A the transducer is separated from the housing 33 with O-rings 35. The housing is separated from the transverse pipe section 34 with other O-rings 36.

FIG. 2C illustrates the positioning of the non-intrusive interferometric sensor transducer shown in FIG. 1C. The transducer 2,14,43 is clamped with an elastic rubber band 41 to the pipe wall 45 in a bend of a flow loop with the water and sand flowing in the direction of the arrow. The transducer consists of a plastic cap 43 outside a steel section 14 with the fibre 2 wrapped around it in a groove. The material of the fibre coil section is Torlon, which is a plastic material chosen to enhance the radial expansion due to the acoustic pressure wave. Other materials can be used, including steel.

FIGS. 3A–C shows a schematic illustration of the optical sensor system using a fibre optic interferometer in combination with a highly coherent fibre distributed feedback (DFB) lasers, where the laser is either used as the sensing elements with interferometric readout (FIG. 3A), or as a source for reading out an interferometric fibre coil sensors, as illustrated in FIGS. 3B and 3C.

As illustrated in FIG. 3A the optical fibre 3 can be an active fibre laser or partially be such a laser, typically a fibre DFB laser 55, where a change in optical path length will cause a modulation of the laser frequency, which can be converted to a detectable intensity modulation by a receiving interferometer, in this example comprising a pump laser 51, a connector 52, a detector 53 as well as a well known fibre interferometer 54, e.g. a Michelson interferometer, with a PZT phase modulator 57 and a fibre coil 58. A change in birefringence can be detected by measuring the beat frequency between the two orthogonally polarised laser frequencies of a dual-polarisation fibre DFB laser 55.

Alternatively the optical fibre 3 in the sensor can be part of an optical interferometer 54, as illustrated in FIG. 3B, where a change in optical path length and/or birefringence in the fibre coil 2 can cause a modulation of the light intensity at the output of the interferometer 54 when the interferometer is illuminated by a light source 51,55, typically a high coherence laser such as a fibre DFB laser. Typically the optical fibre 3 will be fibre coil 2 wrapped around the transducer element.

Alternatively the interferometer in the optical fibre 3 in the sensor can be a passive fibre Bragg grating (FBG) or part of such a grating, as illustrated in FIG. 3C, where a change in optical path length and/or birefringence can cause a modulation of the light intensity of the reflected light from the grating 56 when the grating is illuminated by a light source 51, 55, typically a high coherence laser such as a fibre DFB laser 55. The grating can include a phase-shift that provides a sharp dip in the reflection spectrum. When the laser wavelength is positioned at the steep edge of this dip the magnitude of the modulated reflected light intensity will be greatly enhanced, hence enhancing the resolution.

Several fibre optic sensor elements, either interferometric sensors, laser sensors, or FBG sensors attached to or embedded in separate mechanical transducer elements, can be multiplexed along one optical fibre. The readout instrumentation and signal processing can be placed several kilometers from the sensor elements linked by a single optical fibre.

FIG. 4A shows the measured signal time response of the non-intrusive fibre interferometric sensor transducer shown in FIG. 1C when a single sand particle is hitting the inside of the steel bend. The corresponding PZT transducer signal is shown for comparison. We see that the signals are quite similar, as are also the signal-to-noise ratios. FIGS. 4B and 4C shows the corresponding frequency spectra and also the spectra with a sand-free flow. For both the PZT and the fibre optic probe the signals are strongest between 100 and 300 kHz, related to mechanical resonances in the pipe wall, and also the angle and position of the sand particle hit. At these high frequencies the sand induced signals will dominate over other noise sources to provide a good signal-to-noise ratio.

FIG. 5A shows the measured signal time response with the intrusive fibre interferometric sensor transducer shown in FIG. 1B. FIG. 5B shows the corresponding frequency spectrum with maxima in the frequency range of 250–300 kHz. The expected resonance frequency as discussed under FIG. 1 is ca. 310 kHz.

FIGS. 6A and 6B show the time response and corresponding frequency response of the intrusive fibre laser probe shown in FIG. 1A. From the time response in FIG. 6A the signal-to-noise ratio is seen to be very high. The main resonance is around 80 kHz.

The invention claimed is:

1. Fibre optic particle detector for measurements in a fluid flow, comprising:
   a transducer element;
   an optical fibre;
   an optical interferometer; and
   an optical light source providing light in said fiber,
   the optical fiber being attached to the transducer element,
   wherein the transducer element is arranged to be hit by particles moving in the flow by exposing part of said transducer element to the flowing fluid, each particle hitting the exposed part thus generating acoustic waves propagating some distance in the transducer element to the optical fibre.

2. Particle detector according to claim 1, wherein the light source comprises the optical fibre at least partially constituting an active fibre laser.

3. Particle detector according to claim 2, wherein the active fibre laser comprises a fibre DFB laser.

4. Particle detector according to claim 1, wherein the light source comprises a high coherence laser.

5. Particle detector according to claim 4, wherein the high coherence laser comprises a fibre DFB laser.

6. Particle detector according to claim 1, wherein the optical fibre is part of the optical interferometer, wherein a change in optical path length resulting from the coupled acoustic waves causes modulations of a light intensity at an output of the interferometer.

7. Particle detector according to claim 1, wherein the optical fibre is part of the optical interferometer, wherein a change in birefringence resulting from the coupled acoustic waves causes modulations of a light intensity at an output of the interferometer.

8. Particle detector according to claim 1, wherein the optical fibre comprises at least part of a passive fibre Bragg grating (FBG), wherein said light source is coupled to the optical fibre and illuminates said grating.

9. Particle detector according to claim 8, wherein said grating includes a phase-shift providing a sharp dip in a reflection spectrum, wherein, when a laser wavelength is positioned at a steep edge of this dip, a magnitude of a modulated reflected light intensity will be greatly enhanced, hence enhancing a resolution of the detector.

10. Particle detector according to claim 1, comprising several fibre optic sensor elements and separate mechanical transducer elements coupled thereto.

11. Particle detector according to claim 10, wherein the fibre optic sensor elements are selected from interferometric sensors, laser sensors, and FBG sensors.

12. Particle detector according to claim 1, arranged to project at least partially into a conduit carrying the fluid flow, transversally to the fluid flow.

13. Particle detector according to claim 12, being arranged to project into the fluid flow at an angle selected from 90 degrees and 45 degrees.

14. Particle detector according to claim 12, comprising sealing means to sealingly fix the detector within said conduit.

15. Particle detector according to claim 14, wherein the sealing means substantially decouples the detector acoustically from the conduit.

16. An assembly comprising a particle detector according to claim 1, and a conduit carrying said fluid flow.

17. An assembly according to claim 16, wherein the particle detector is located at a bend of the conduit.

18. An assembly according to claim 16, wherein the particle detector is located near a bend of the conduit.

19. Fibre optic particle detector for measurements in a fluid flow, comprising:
   a transducer element;
   an optical fibre;
   an optical interferometer; and
   an optical light source providing light in said fiber,
   the optical fiber being embedded in the transducer element,
   wherein the transducer element is arranged to be hit by particles moving in the flow by exposing part of said transducer element to the flowing fluid, each particle hitting the exposed part thus generating acoustic waves propagating some distance in the transducer element to the optical fibre.

20. Particle detector according to claim 19, wherein the light source comprises the optical fibre at least partially constituting an active fibre laser.

21. Particle detector according to claim 20, wherein the active fibre laser comprises a fibre DFB laser.

22. Particle detector according to claim 19, wherein the light source comprises a high coherence laser.

23. Particle detector according to claim 22, wherein the high coherence laser comprises a fibre DFB laser.

24. Particle detector according to claim 19, wherein the optical fibre is part of the optical interferometer, wherein a change in optical path length resulting from the coupled acoustic waves causes modulations of a light intensity at an output of the interferometer.

25. Particle detector according to claim 19, wherein the optical fibre is part of the optical interferometer, wherein a change in birefringence resulting from the coupled acoustic waves causes modulations of a light intensity at the output of the interferometer.

26. Particle detector according to claim 19, wherein the optical fibre comprises at least part of a passive fibre Bragg grating (FBG), wherein said light source is coupled to the optical fibre and illuminates said grating.

27. Particle detector according to claim 26, wherein said grating includes a phase-shift providing a sharp dip in a reflection spectrum, wherein, when a laser wavelength is positioned at a steep edge of this dip, a magnitude of a modulated reflected light intensity will be greatly enhanced, hence enhancing a resolution of the detector.

28. Particle detector according to claim 19, comprising several fibre optic sensor elements and separate mechanical transducer elements coupled thereto.

29. Particle detector according to claim 28, wherein the fibre optic sensor elements are selected from interferometric sensors, laser sensors, and FBG sensors.

30. Particle detector according to claim 19, arranged to project at least partially into a conduit carrying the fluid flow, transversally to the fluid flow.

31. Particle detector according to claim 30, being arranged to project into the fluid flow at an angle selected from 90 degrees and 45 degrees.

32. Particle detector according to claim 30, comprising sealing means to sealingly fix the detector within said conduit.

33. Particle detector according to claim 32, wherein the sealing means substantially decouples the detector acoustically from the conduit.

34. An assembly comprising a particle detector according to claim 19, and a conduit carrying said fluid flow.

35. An assembly according to claim 34, wherein the particle detector is located at a bend of the conduit.

36. An assembly according to claim 34, wherein the particle detector is located near a bend of the conduit.

37. Fibre optic particle detector for measurements in a fluid flow, comprising:
   a transducer element;
   a mechanical structure in acoustic contact with the transducer element;
   an optical fibre;
   an optical interferometer; and
   an optical light source providing light in said fiber,
   the optical fiber being attached to the transducer element,
   wherein said mechanical structure is arranged to be hit by particles moving in the flow by exposing part of said mechanical structure to the flowing fluid, each particle hitting the exposed part thus generating acoustic waves propagating some distance in the mechanical structure to the optical fibre.

38. Particle detector according to claim 37, wherein at least a part of the mechanical structure has a circular cross section around which the optical fibre is coiled.

39. Particle detector according to claim 38, wherein the mechanical structure is formed with a groove at said circular cross section.

40. Particle detector according to claim 37, wherein the light source comprises the optical fibre at least partially constituting an active fibre laser.

41. Particle detector according to claim 40, wherein the active fibre laser comprises a fibre DFB laser.

42. Particle detector according to claim 37, wherein the light source comprises a high coherence laser.

43. Particle detector according to claim 42, wherein the high coherence laser comprises a fibre DFB laser.

44. Particle detector according to claim 37, wherein the optical fibre is part of the optical interferometer, wherein a change in optical path length resulting from the coupled acoustic waves causes modulations of a light intensity at an output of the interferometer.

45. Particle detector according to claim 37, wherein the optical fibre is part of the optical interferometer, wherein a change in birefringence resulting from the coupled acoustic waves causes modulations of a light intensity at an output of the interferometer.

46. Particle detector according to claim 37, wherein the optical fibre comprises at least part of a passive fibre Bragg grating (FBG), wherein said light source is coupled to the optical fibre and illuminates said grating.

47. Particle detector according to claim 46, wherein said grating includes a phase-shift providing a sharp dip in a reflection spectrum, wherein, when a laser wavelength is positioned at a steep edge of this dip, a magnitude of a modulated reflected light intensity will be greatly enhanced, hence enhancing a resolution of the detector.

48. Particle detector according to claim 37, comprising several fibre optic sensor elements coupled to separate mechanical transducer elements.

49. Particle detector according to claim 48, wherein the fibre optic sensor elements are selected from interferometric sensors, laser sensors and FBG sensors.

50. Particle detector according to claim 37, arranged to project at least partially into a conduit carrying the fluid flow, transversally to the fluid flow.

51. Particle detector according to claim 50, being arranged to project into the fluid flow at an angle selected from 90 degrees and 45 degrees.

52. Particle detector according to claim 37, comprising means for mounting the particle detector to an outer surface of a conduit.

53. An assembly comprising a particle detector according to claim 37, and a conduit carrying said fluid flow.

54. An assembly according to claim 53, wherein the particle detector is located at a bend of the conduit.

55. An assembly according to claim 53, wherein the particle detector is located near a bend of the conduit.

56. Fibre optic particle detector for measurements in a fluid flow, comprising:
   a transducer element;
   a mechanical structure in acoustic contact with the transducer element;
   an optical fibre;
   an optical interferometer; and an optical light source providing light in said fiber, the optical fiber being embedded in the transducer element, wherein said mechanical structure is arranged to be hit by particles moving in the flow by exposing part of said mechanical structure to the flowing fluid, each particle hitting the exposed part thus generating acoustic waves propagating some distance in the mechanical structure to the optical fibre.

57. Particle detector according to claim 56, wherein the mechanical structure comprises a rod having a longitudinal hole, the optical fibre being positioned in said hole.

58. Particle detector according to claim 56, wherein the light source comprises the optical fibre at least partially constituting an active fibre laser.

59. Particle detector according to claim 58, wherein the active fibre laser comprises a fibre DFB laser.

60. Particle detector according to claim 56, wherein the light source comprises a high coherence laser.

61. Particle detector according to claim 60, wherein the high coherence laser comprises a fibre DFB laser.

62. Particle detector according to claim 56, wherein the optical fibre is part of the optical interferometer, wherein a change in optical path length resulting from the coupled acoustic waves causes modulations of a light intensity at an output of the interferometer.

63. Particle detector according to claim 56, wherein the optical fibre is part of the optical interferometer, wherein a change in birefringence resulting from the coupled acoustic waves causes modulations of a light intensity at an output of the interferometer.

64. Particle detector according to claim 56, wherein the optical fibre comprises at least part of a passive fibre Bragg grating (FBG), wherein said light source is coupled to the optical fibre and illuminates said grating.

65. Particle detector according to claim 64, wherein said grating includes a phase-shift providing a sharp dip in a reflection spectrum, wherein, when a laser wavelength is positioned at a steep edge of this dip, a magnitude of a modulated reflected light intensity will be greatly enhanced, hence enhancing a resolution of the detector.

66. Particle detector according to claim 56, comprising several fibre optic sensor elements coupled to separate mechanical transducer elements.

67. Particle detector according to claim 66, wherein the fibre optic sensor elements are selected from interferometric sensors, laser sensors and FBG sensors.

68. Particle detector according to claim 56, arranged to project at least partially into a conduit carrying the fluid flow, transversally to the fluid flow.

69. Particle detector according to claim 68, being arranged to project into the fluid flow at an angle selected from 90 degrees and 45 degrees.

70. An assembly comprising a particle detector according to claim 56, and a conduit carrying said fluid flow.

71. An assembly according to claim 70, wherein the particle detector is located at a bend of the conduit.

72. An assembly according to claim 70, wherein the particle detector is located near a bend of the conduit.

73. A method of detecting particles in a fluid flow, comprising:

providing a fibre optic particle detector according to claim 1;

permitting particles to hit the exposed part; and detecting acoustic waves generated by particles hitting said exposed part by detecting an output of the optical interferometer.

74. Fibre optic particle detector for measurements in a fluid flow, comprising:

a transducer element;

an optical fibre;

an optical interferometer; and an optical light source providing light in said fiber, the optical fiber being at least one of attached to, or embedded in, the transducer element, wherein the transducer element is arranged to be hit by particles moving in the flow by exposing part of said transducer element to the flowing fluid, each particle hitting the exposed part thus generating acoustic waves propagating some distance in the transducer element to the optical fibre.

* * * * *